(12) United States Patent
Yu et al.

(10) Patent No.: US 8,367,821 B2
(45) Date of Patent: Feb. 5, 2013

(54) PREPARATION OF ESLICARBAZEPINE AND RELATED COMPOUNDS BY ASYMMETRIC HYDROGENATION

(75) Inventors: Bing Yu, Ambler, PA (US); Wenge Li, Plainsboro, NJ (US); David Alexander Learmonth, Alfena (PT)

(73) Assignee: BIAL—Portela & C.A., S.A., S. Mamede do Coronado (PT)

( * ) Notice: Subject to any disclaimer, the term of this patent is extended or adjusted under 35 U.S.C. 154(b) by 519 days.

(21) Appl. No.: 12/294,855

(22) PCT Filed: Apr. 11, 2007

(86) PCT No.: PCT/PT2007/000017
§ 371 (c)(1),
(2), (4) Date: Mar. 11, 2010

(87) PCT Pub. No.: WO2007/117166
PCT Pub. Date: Oct. 18, 2007

(65) Prior Publication Data
US 2010/0173893 A1  Jul. 8, 2010

(30) Foreign Application Priority Data
Apr. 11, 2006 (GB) .................................. 0607317.5

(51) Int. Cl.
C07D 223/22 (2006.01)
(52) U.S. Cl. ....................................................... 540/589
(58) Field of Classification Search .................. 540/589
See application file for complete search history.

(56) References Cited

U.S. PATENT DOCUMENTS
5,753,646 A    5/1998  Benes et al.
2004/0044200 A1 *  3/2004  Gutman et al. ............... 540/590

FOREIGN PATENT DOCUMENTS
EP    1308435 A2    5/2003
WO    02092572 A1   11/2002
WO    2004031155 A1  4/2004
WO    2004087168 A1  10/2004
WO    2007117166 A1  10/2007

OTHER PUBLICATIONS

Benes, Jan, et al., "Anticonvulsant and sodium channel-blocking properties of novel 10,11-dihydro-5H-dibenz[b,f] azepine-5-carboxamide derivatives," J. Med. Chem, 1999, pp. 2582-2587, vol. 42, No. 14.
Grant, Susan M., et al., "Oxcarbazepine, A review of its pharmacology and therapeutic potential in epilepsy, trigeminal neuralgia and affective disorders," Drugs, 1992, pp. 873-888, vol. 43, No. 6, Adis International Limited, Auckland, New Zealand.
Heckendorn, Roland, "Synthesis of trans-10,11-dihydro-10,11-dihydroxy-5H-dibenz[b,f]azepine-5-carboxamide, a major metabolite of carbamazepine," Helvetica Chimica Acta, 1987, pp. 1955-1962, vol. 70.

(Continued)

Primary Examiner — Brenda Coleman
(74) Attorney, Agent, or Firm — Conley Rose, P.C.; Rodney B. Carroll

(57) ABSTRACT

A process for preparing a compound of the formula IA or IB:

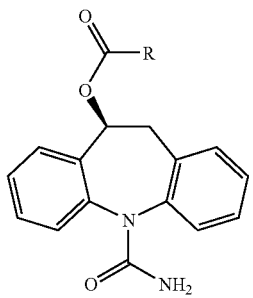

IA

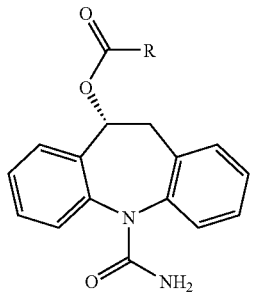

IB wherein R is alkyl, aminoalkyl, halogenalkyl, aralkyl, cycloalkyl, cycloalkylalkyl, alkoxy, phenyl or substituted phenyl or pyridyl group; the term alkyl means carbon chain, straight or branched, containing from 1 to 18 carbon atoms; the term halogen represents fluorine, chlorine, bromine or iodine; the term cycloalkyl represents a saturated alicyclic group with 3 to 6 carbon atoms; the term aryl represents unsubstituted phenyl group or phenyl substituted by alkoxy, halogen or nitro group, the process comprising asymmetric hydrogenation of a compound of the formula II:

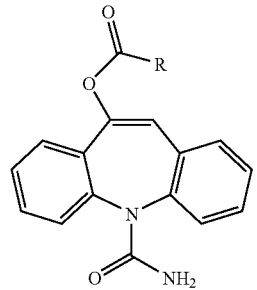

II wherein R has the same meanings as above, using a chiral catalyst and a source of hydrogen.

34 Claims, No Drawings

OTHER PUBLICATIONS

Schutz, H., et al., "The metabolism of 14C-oxcarbazepine in man," Xenobiotica, 1986, pp. 769-778, vol. 16, No. 8.

Volosov, Andrew, et al., "Comparative stereoselective pharmacokinetic analysis of 10-hydroxycarbazepine after oral administration of its individual enantiomers and the racemic mixture to dogs," Epilepsia, 2000, pp. 1107-1111, vol. 41, No. 9, Lippincott Williams & Wilkins, Inc., Baltimore.

Foreign communication from the priority application—Search Report, Application GB0607317.5, Aug. 9, 2006, 3 pages.

Foreign communication from the priority application—International Preliminary Report on Patentability, PCT/PT2007/000017, Oct. 14, 2008, 7 pages.

Foreign communication from the priority application—International Search Report and Written Opinion, PCT/PT2007/000017, Aug. 20, 2007, 10 pages.

* cited by examiner

PREPARATION OF ESLICARBAZEPINE AND RELATED COMPOUNDS BY ASYMMETRIC HYDROGENATION

CROSS-REFERENCE TO RELATED APPLICATIONS

This application is a filing under 35 U.S.C. 371 of International Application No. PCT/PT2007/000017 filed Apr. 11, 2007, entitled "Preparation of Eslicarbazepine and Related Compounds by Asymmetric Hydrogenation," claiming priority of Great Britian Patent Application No. 0607317.5 filed Apr. 11, 2006, which applications are incorporated by reference herein in their entirety.

FIELD OF THE INVENTION

This invention relates to the synthesis of enantiomeric dibenz/b,f/azepine derivatives. More particularly, the present invention relates to the asymmetric hydrogenation of enol substrates in the synthesis of enantiomeric dibenz/b,f/azepine derivatives, in particular, to a process for preparing eslicarbazepine acetate ((S)-(−)-10-acetoxy-10,11-dihydro-5H-dibenz/b,f/azepine-5-carboxamide) and R-(+)-licarbazepine acetate ((R)-(+)-10-acetoxy-10,11-dihydro-5H-dibenz/b,f/azepine-5-carboxamide) and their derivatives by asymmetric hydrogenation of the corresponding enol acetate or of the corresponding enol ester derivative.

BACKGROUND OF THE INVENTION

In recent years, there has been a significant change in the way that chiral compounds are viewed within the pharmaceutical industry. In the past, many molecules containing asymmetric centres were launched onto the drug marketplace as racemic mixtures. Subsequent concerns as to the safety and/or efficacy of such racemic drugs have persuaded the industry to research and develop single stereoisomer drugs. These concerns were based on the concept that racemic drugs could be considered to be 50% impure, since one isomer of a given racemic mixture is often pharmacologically inactive or significantly less active than the other isomer; indeed, one isomer may exert a different action or give origin to unwanted side-effects. Isomeric compounds may undergo different metabolic processes which complicate pharmacokinetic issues further. Consequently, drug regulatory authorities have become increasingly more cautious and frequently demand concise information on the properties and behaviour of individual isomers.

A particularly interesting example in this respect is the case of oxcarbazepine (OXC), the 10-keto analogue of carbamazepine (CBZ).

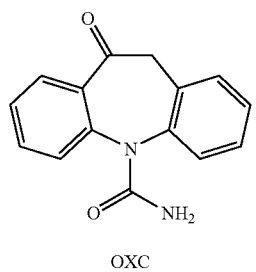

OXC

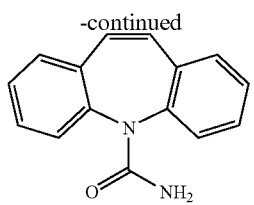

CBZ

These two compounds are structurally very similar and are currently used in the treatment of epilepsy. Oxcarbazepine was designed to avoid the oxidative metabolic transformation of CBZ and is claimed to be a better tolerated drug (Grant, S. M. et al., Drugs, 43, 873-888 (1992)). However oxcarbazepine undergoes rapid and complete metabolism in vivo to the racemic 10-hydroxy derivative of oxcarbazepine, called "MHD" (see (±)-MHD, Schutz, H. et al., Xenobiotica, 16(8), 769-778 (1986)) and therefore represents an apparently achiral drug which undergoes metabolic transformation to give a mixture of two pharmacologically active enantiomers.

The synthesis and improved anticonvulsant properties of (S)-(−)-10-acetoxy-10,11-dihydro-5H-dibenz/b,f/azepine-5-carboxamide (eslicarbazepine acetate), and (R)-(+)-10-acetoxy-10,11-dihydro-5H-dibenz/b,f/azepine-5-carboxamide (R-(+)-licarbazepine acetate), both single-isomer drugs specifically designed to avoid such formation of racemic mixtures of active metabolites have been described (Benes, J. et al., U.S. Pat. No. 5,753,646 and Benes, J. et al., J. Med. Chem., 42, 2582-2587 (1999)). The key step of the synthesis of compounds eslicarbazepine acetate and R-(+)-licarbazepine acetate involves the resolution of racemic 10,11-dihydro-10-hydroxy-5H-dibenz/b,f/azepine-5-carboxamide ((±)-MHD) into its separate, optically pure stereoisomers, (S)-(+)-10,11-dihydro-10-hydroxy-5H-dibenz/b,f/azepine-5-carboxamide ((S)-(+)-MHD), and (R)-(−)-10,11-dihydro-10-hydroxy-5H-dibenz/b,f/azepine-5-carboxamide ((R)-(−)-MHD), which are the principal intermediates.

Both stereoisomers of MHD are known compounds and are commonly used as standards in studies of oxcarbazepine metabolism. Additionally, MHD is a sodium channel blocker, and has potential efficacy in the treatment of acute manic episodes of bipolar I disorders.

The resolution of the racemic alcohol, (±)-MHD, has been previously described in the chemical literature (Benes, J. et al., J. Med. Chem., 42, 2582-2587 (1999) and Volosov, A. et al., Epilepsia, 41(9), 1107-1111 (2000)). These methods involve the formation of diastereoisomeric menthoxyacetate-ester derivatives of (±)-MHD; by taking advantage of the different solubilities of these diastereoisomeric esters, separation is possible by fractional crystallisation and subsequent hydrolysis affords the individually pure stereoisomers, (S)-(+)-MHD and (R)-(−)-MHD. However, this method was utilised for the preparation of only rather small quantities of each stereoisomer and contains certain inherent disadvantages which preclude its use for the preparation of pilot-scale quantities and thereafter industrial production. The necessary optically pure resolving agents, (+) and (−)-menthoxyacetic acid are extremely expensive and are not readily available in sufficiently large quantities from commercial sources. Their preparation from cheaper, readily available optically pure (+) or (−)-menthol could be considered, but this preparation is tedious, slow and potentially dangerous. Furthermore, these menthoxyacetic acids require 'activation' in order to react with (±)-MHD and form the key intermediate diastereoisomeric menthoxyacetate esters. This activation is normally achieved via conversion of the free acids to the acid chlorides (these acid chlorides are again very expensive products from commercial sources), an extra synthetic step which requires the use of unpleasant halogenating reagents such as for example thionyl chloride or oxalyl chloride. Alternatively, this reaction can be accomplished using a coupling reagent such as for example dicyclohexylcarbodiimide. This reagent is also expensive; additionally it is difficult to manipulate due to its low melting point and is indicated as a potent skin irritant, thus posing health risks for workers. Often there are encountered difficulties in removing completely the dicyclohexylurea by-product from the wanted product. A further and very serious limitation of this method is the relatively low yield obtained of the optically pure menthoxyacetate ester which is isolated after crystallisation, in yields usually only marginally better than 20% (the maximum yield being 50% for each isomer).

WO02/092572 discloses a process for separating the stereoisomers of (S)-(+)-MHD and (R)-(−)-MHD from the racemic mixture by means of a process which involves the use of an appropriate tartaric acid anhydride to resolve the stereoisomers. In particular, the (2R,3R)-di-O,O'-substituted-tartaric acid anhydride can be used to precipitate the diastereoisomeric precursor of (S)-(+)-MHD, and the (2S,3S)-di-O,O'-substituted-tartaric acid anhydride can be used to precipitate the diastereoisomeric precursor of (R)-(−)-MHD. eslicarbazepine acetate and R-(+)-licarbazepine acetate may be obtained from the resolved (S)-(+)-MHD and (R)-(−)-MHD by acylation.

The dibenz/b,f/azepine derivatives of particular interest in the present invention are the compounds with the following chemical formula:

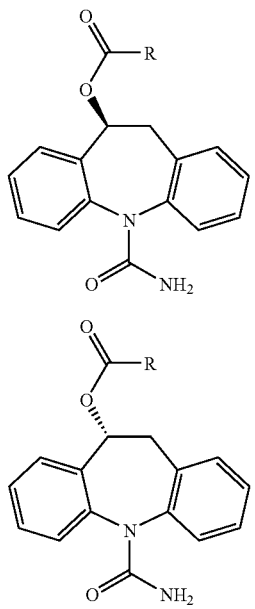

wherein R is alkyl, aminoalkyl, halogenalkyl, aralkyl, cycloalkyl, cycloalkylalkyl, alkoxy, phenyl or substituted phenyl or pyridyl group; the term alkyl means carbon chain, straight or branched, containing from 1 to 18 carbon atoms; the term halogen represents fluorine, chlorine, bromine or iodine; the term cycloalkyl represents a saturated alicyclic group with 3 to 6 carbon atoms; the term aryl represents unsubstituted phenyl group or phenyl substituted by alkoxy, halogen or nitro group. Compounds of formula IA and IB are disclosed in U.S. Pat. No. 5,753,646.

SUMMARY OF THE INVENTION

It is an object of the present invention to provide an improved process for preparing eslicarbazepine acetate and R-(+)-licarbazepine acetate, and improved processes for preparing dibenz/b,f/azepine derivatives of formula IA and IB, in general.

DETAILED DESCRIPTION OF THE INVENTION

According to a first aspect of the present invention, there is provided a process for preparing a compound of the formula IA or IB:

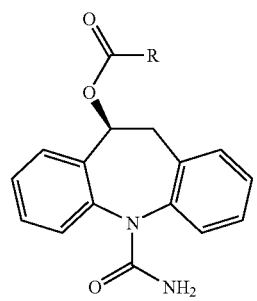

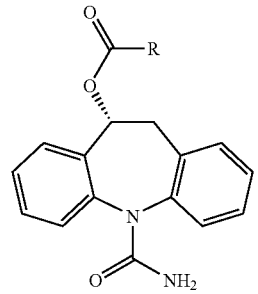

wherein R is alkyl, aminoalkyl, halogenalkyl, aralkyl, cycloalkyl, cycloalkylalkyl, alkoxy, phenyl or substituted phenyl or pyridyl group; the term alkyl means carbon chain, straight or branched, containing from 1 to 18 carbon atoms; the term halogen represents fluorine, chlorine, bromine or iodine; the term cycloalkyl represents a saturated alicyclic group with 3 to 6 carbon atoms; the term aryl represents unsubstituted phenyl group or phenyl substituted by alkoxy, halogen or nitro group, the process comprising asymmetric hydrogenation of a compound of the formula II:

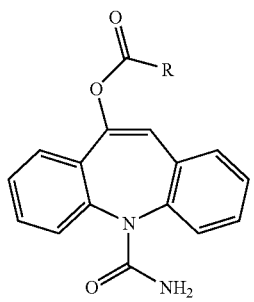

wherein R has the same meanings as above, using a chiral catalyst and a source of hydrogen.

In an embodiment, R is $C_1$ to $C_3$ alkyl, preferably methyl.

In another embodiment, the compound of formula IA or IB is the S or R enantiomer, respectively, of:

(1) 10-acetoxy-10,11-dihydro-5H-dibenz/b,f/azepine-5-carboxamide
(2) 10-benzoyloxy-10,11-dihydro-5H-dibenz/b,f/azepine-5-carboxamide
(3) 10-(4-methoxybenzoyloxy)-10,11-dihydro-5H-dibenz/b,f/azepine-5-carboxamide
(4) 10-(3-methoxybenzoyloxy)-10,11-dihydro-5H-dibenz/b,f/azepine-5-carboxamide
(5) 10-(2-methoxybenzoyloxy)-10,11-dihydro-5H-dibenz/b,f/azepine-5-carboxamide
(6) 10-(4-nitrobenzoyloxy)-10,11-dihydro-5H-dibenz/b,f/azepine-5-carboxamide
(7) 10-(3-nitrobenzoyloxy)-10,11-dihydro-5H-dibenz/b,f/azepine-5-carboxamide
(8) 10-(2-nitrobenzoyloxy)-10,11-dihydro-5H-dibenz/b,f/azepine-5-carboxamide
(9) 10-(4-chlorobenzoyloxy)-10,11-dihydro-5H-dibenz/b,f/azepine-5-carboxamide
(10) 10-(3-chlorobenzoyloxy)-10,11-dihydro-5H-dibenz/b,f/azepine-5-carboxamide
(11) 10-(2-acetoxybenzoyloxy)-10,11-dihydro-5H-dibenz/b,f/azepine-5-carboxamide
(12) 10-propionyloxy-10,11-dihydro-5H-dibenz/b,f/azepine-5-carboxamide
(13) 10-butyryloxy-10,1-dihydro-5H-dibenz/b,f/azepine-5-carboxamide
(14) 10-pivaloyloxy-10,11-dihydro-5H-dibenz/b,f/azepine-5-carboxamide
(15) 10-[(2-propyl)pentanoyloxy]-10,11-dihydro-5H-dibenz/b,f/azepine-5-carboxamide
(16) 10-[(2-ethyphexanoyloxy]-10,11-dihydro-5H-dibenz/b,f/azepine-5-carboxamide
(17) 10-stearoyloxy-10,11-dihydro-5H-dibenz/b,f/azepine-5-carboxamide
(18) 10-cyclopentanoyloxy-10,11-dihydro-5H-dibenz/b,f/azepine-5-carboxamide
(19) 10-cyclohexanoyloxy-10,11-dihydro-5H-dibenz/b,f/azepine-5-carboxamide
(20) 10-phenylacetoxy-10,11-dihydro-5H-dibenz/b,f/azepine-5-carboxamide
(21) 10-(4-methoxyphenyl)acetoxy-10,11-dihydro-5H-dibenz/b,f/-azepine-5-carboxamide
(22) 10-(3-methoxyphenyl)acetoxy-10,11-dihydro-5H-dibenz/b,f/azepine-5-carboxamide
(23) 10-(4-nitrophenyl)acetoxy-10,11-dihydro-5H-dibenz/b,f/azepine-5-carboxamide
(24) 10-(3-nitrophenyl)acetoxy-10,11-dihydro-5H-dibenz/b,f/azepine-5-carboxamide
(25) 10-nicotinoyloxy-10,11-dihydro-5H-dibenz/b,f/azepine-5-carboxamide
(26) 10-isonicotinoyloxy-10,11-dihydro-5H-dibenz/b,f/azepine-5-carboxamide
(27) 10-chloroacetoxy-10,11-dihydro-5H-dibenz/b,f/azepine-5-carboxamide
(28) 10-bromoacetoxy-10,11-dihydro-5H-dibenz/b,f/azepine-5-carboxamide
(29) 10-formyloxy-10,11-dihydro-5H-dibenz/b,f/azepine-5-carboxamide
(30) 10-ethoxycarbonyloxy-10,11-dihydro-5H-dibenz/b,f/azepine-5-carboxamide
(31) 10-(2-chloropropionyloxy)-10,11-dihydro-5H-dibenz/b,f/azepine-5-carboxamide Thus, the present invention provides a process for preparing (S)-(−)-10-acetoxy-10,11-dihydro-5H-dibenz/b,f/azepine-5-carboxamide (eslicarbazepine acetate) from the corresponding enol acetate. The present invention also provides a process for preparing (R)-(+)-10-acetoxy-10,11-dihydro-5H-dibenz/b,f/azepine-5-carboxamide) (R-(+)-licarbazepine acetate) from the corresponding enol acetate.

In an embodiment, the chiral catalyst is a complex of rhodium. Suitably, the chiral catalyst is selected from Rh(I) complexes having chiral ligands with the following structures:

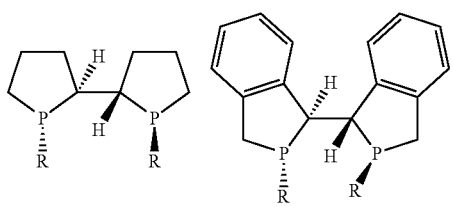

and their stereosiomers, wherein R is selected from alkyl, aryl, substituted alkyl, substituted aryl, hetereoaryl, ferrocenyl, alkoxy and aryloxy. R may be selected from $CH_3$, Et, i-Pr, t-Bu, 1-adamantyl, $Et_3C$, cyclo-$C_5H_9$, cyclo-$C_6H_{11}$, phenyl, p-tolyl, 3,5-dimethylphenyl, 3,5-di-t-butylphenyl, ortho-anisyl and naphthyl. Preferably, R is t-Bu.

In an embodiment, the chiral catalyst is selected from a stereoisomer of [Rh(NBD)(DuanPhos)]$BF_4$, [Rh(COD)(DuanPhos)]$BF_4$, [Rh(NBD)(TangPhos)]$BF_4$ and [Rh(COD)(TangPhos)]$BF_4$, wherein COD is η-1,5-cyclooctadiene, NBD is norbornadiene, and the ScRp-DuanPhos and RRSS-TangPhos stereosiomers have the following chemical structures:

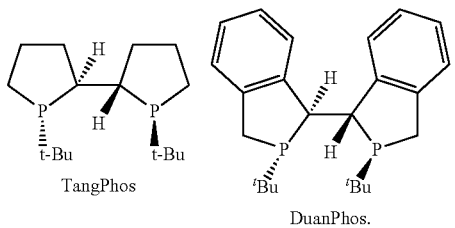

TangPhos

DuanPhos.

More particularly, the chiral catalyst is selected from [Rh(NBD)(SSRR-TangPhos)]$BF_4$, [Rh(COD)(SSRR-TangPhos)]$BF_4$, [Rh(NBD)(RcSp-DuanPhos)]$BF_4$, [Rh(NBD)(ScRp-DuanPhos)]$BF_4$, [Rh(COD)(RcSp-DuanPhos)]$BF_4$, [Rh(NBD)(RRSS-TangPhos)]$BF_4$, [Rh(COD)(RRSS-TangPhos)]$BF_4$ and [Rh(COD)(ScRp-DuanPhos)]$BF_4$.

In an embodiment, the source of hydrogen is hydrogen gas.

In another embodiment, the molar ratio of compound II to catalyst is from 1:1 to 50,000:1, preferably 500:1, more preferably 50:1.

The asymmetric hydrogenation may be carried out at a temperature from 0° C. to room temperature. Suitably, the asymmetric hydrogenation is carried out at room temperature.

In an embodiment, the asymmetric hydrogenation is carried out at a pressure of 20 psi to 1000 psi, preferably 750 psi to 1000 psi.

In another embodiment, the compound of formula II is dissolved in a solvent selected from methanol, ethanol, THF, 2-methyl-THF, methyl acetate, ethyl acetate, dichloromethane, trifluoroethanol, 1,4-dioxane, DMF and mixtures thereof.

In an embodiment, the catalyst is Rh(NBD)(SSRR-TangPhos)BF$_4$ and the solvent is ethyl acetate.

In an alternative embodiment, the catalyst is [Rh(NBD)(RcSp-DuanPhos)]BF$_4$ or [Rh(NBD)(ScRp-DuanPhos)]BF$_4$ and the solvent is ethyl acetate, THF or dichloromethane.

In yet another embodiment, the catalyst is [Rh(COD)(RcSp-DuanPhos)]BF$_4$ and the solvent is ethyl acetate, THF, 2-methyl-THF, or a mixture thereof. Typically, the solvent is THF.

In an embodiment, the compound of formula II is prepared from oxcarbazepine. The oxcarbazepine may be reacted with an anhydride of the formula R—C(O)—O—C(O)—R in the presence of a base and a catalyst. R is alkyl, aminoalkyl, halogenalkyl, aralkyl, cycloalkyl, cycloalkylalkyl, alkoxy, phenyl or substituted phenyl or pyridyl group; the term alkyl means carbon chain, straight or branched, containing from 1 to 18 carbon atoms; the term halogen represents fluorine, chlorine, bromine or iodine; the term cycloalkyl represents a saturated alicyclic group with 3 to 6 carbon atoms; the term aryl represents unsubstituted phenyl group or phenyl substituted by alkoxy, halogen or nitro group. Suitably, the base is pyridine and the catalyst is DMAP.

According to a second aspect of the present invention, there is provided a compound of the formula II:

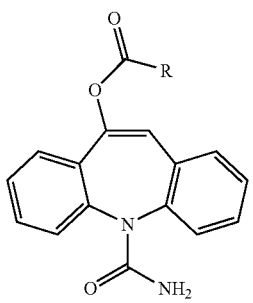

II wherein R is alkyl, aminoalkyl, halogenalkyl, aralkyl, cycloalkyl, cycloalkylalkyl, alkoxy, phenyl or substituted phenyl or pyridyl group; the term alkyl means carbon chain, straight or branched, containing from 1 to 18 carbon atoms; the term halogen represents fluorine, chlorine, bromine or iodine; the term cycloalkyl represents a saturated alicyclic group with 3 to 6 carbon atoms; the term aryl represents unsubstituted phenyl group or phenyl substituted by alkoxy, halogen or nitro group.

According to a third aspect of the present invention, there is provided a process for preparing a pharmaceutical composition comprising a compound of formula IA or IB, the process comprising preparing a compound of formula IA or IB as described above and combining the compound of formula IA or IB with one or more pharmaceutically acceptable carriers and/or one or more pharmaceutically acceptable excipients.

According to a fourth aspect of the present invention, there is provided a process for preparing (S)-(+)-MHD or (R)-(−)-MHD comprising preparing a compound of formula IA or IB, respectively, as described above and converting the compound of formula IA to (S)-(+)-MHD, or the compound of formula IB to (R)-(−)-MHD, by deesterification.

According to a fifth aspect of the present invention, there is provided a process for preparing a compound of formula II:

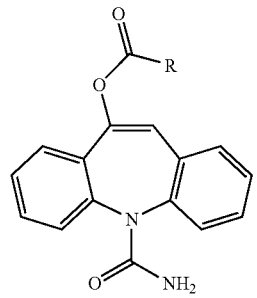

II wherein R is CH$_3$, comprising reacting oxcarbazepine with acetic anhydride in the presence of a base and a catalyst. Suitably, the base is pyridine and the catalyst is DMAP. The present invention provides a novel and efficient process for catalysing the hydrogenation of compounds of formula II to produce compounds of formulas IA or IB in high enantiomeric excess.

The present invention makes use of chiral catalysts, such as Rh(I) complexes having chiral ligands with the following structures:

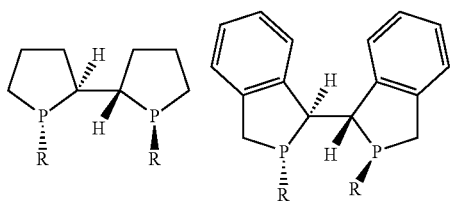

and their stereosiomers, wherein R is selected from alkyl, aryl, substituted alkyl, substituted aryl, hetereoaryl, ferrocenyl, alkoxy and aryloxy. For example, the R groups may be CH$_3$, Et, i-Pr, t-Bu, 1-adamantyl, Et$_3$C, cyclo-C$_5$H$_9$, cyclo-C$_6$H$_{11}$, phenyl, p-tolyl, 3,5-dimethylphenyl, 3,5-di-$^t$butylphenyl, ortho-anisyl and naphthyl.

In particular, the present invention employs the following catalysts, where COD is η-1,5-cyclooctadiene, NBD is norbornadiene, and where the RRSS-TangPhos and ScRp-DuanPhos stereoisomers have the following structures:

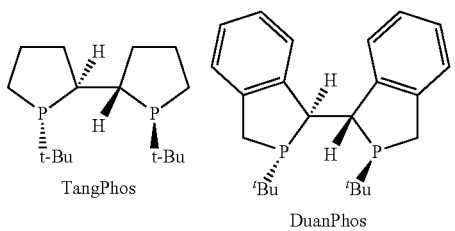

TangPhos     DuanPhos

[Rh(NBD)(SSRR-TangPhos)]BF$_4$—produces the S product, i.e. compound IA
[Rh(COD)(SSRR-TangPhos)]BF$_4$—produces the S product, i.e. compound IA
[Rh(NBD)(RcSp-DuanPhos)]BF$_4$—produces the S product, i.e. compound IA
[Rh(COD)(RcSp-DuanPhos)]BF$_4$—produces the S product, i.e. compound IA
[Rh(NBD)(RRSS-TangPhos)]BF$_4$—produces the R product, i.e. compound IB

[Rh(COD)(RRSS-TangPhos)]BF$_4$—produces the R product, i.e. compound IB

[Rh(NBD)(ScRp-DuanPhos)]BF$_4$—produces the R product, i.e. compound IB

[Rh(COD)(ScRp-DuanPhos)]BF$_4$—produces the R product, i.e. compound IB

Rh((RcSp)-DuanPhos)(COD)BF$_4$ and Rh((SSRR)-TangPhos)(COD)BF$_4$ have the following chemical structures.

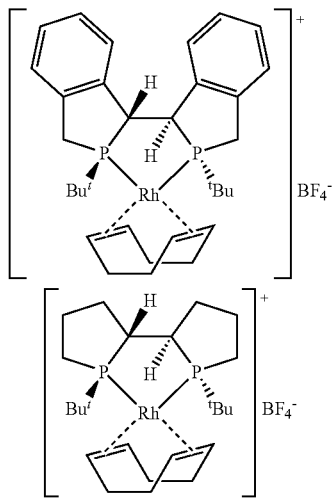

The molar ratio of substrate to catalyst may be from 1:1 to 50,000:1. Preferably 500:1, more preferably 50:1.

The enol substrate has very low solubility in most common solvents. Generally, it dissolves partially in DMF, THF and dichloromethane, less so in ethyl acetate, and it is sparingly soluble in methanol and toluene at room temperature. The solubility of the catalyst should also be considered when choosing the solvent. Furthermore, the choice of solvent affects the enantiomeric excess (ee) of the compound of formula IA and IB. Suitable solvents are those which provide solubility for the enol substrate and catalyst, and give high ee values.

For example, when [Rh(COD)(RcSp-DuanPhos)]BF$_4$ is used as the catalyst, comparable enantioselectivity is exhibited when THF, ethyl acetate and 2-methyl-THF are used as solvents. However, the enol acetate of formula II, when R is methyl, has highest solubility in THF. Thus, THF is the preferred solvent for the particular reaction of the enol acetate of formula II, when R is methyl, and [Rh(COD)(ReSp-DuanPhos)]BF$_4$. Trifluoroethanol is also a good solvent for enol acetate II, when R is methyl, but gives a low enantiomeric excess. Combining it with THF combines the favourable solubility of trifluoroethanol with the high enantiomeric excess of THF, giving rise to an effective solvent mixture.

The source of hydrogen may be hydrogen gas. The hydrogen gas used in the hydrogenation may have a wide range of pressures, suitably from 20 psi to 1000 psi. In the reaction of enol acetate II (when R is methyl) and a solvent of ethyl acetate, THF or mixtures thereof, comparable enantiomeric excesses are obtained when pressures of hydrogen ranging from 20 psi to 1000 psi are employed. However, the enol acetate II has higher activity at higher pressures, so pressures in the top end of the 20 psi to 1000 psi range are preferred, suitably 750 psi to 1000 psi.

The temperature at which the reaction is carried out may be in the range 0° C. to room temperature. The solubility of the enol substrate II decreases with decreasing temperature, so room temperature is the preferred temperature.

The compounds of formula IA and IB prepared according to the present invention include the S and R enantiomers, respectively, of the following:

(1) 10-acetoxy-10,11-dihydro-5H-dibenz/b,f/azepine-5-carboxamide
(2) 10-benzoyloxy-10,11-dihydro-5H-dibenz/b,f/azepine-5-carboxamide
(3) 10-(4-methoxybenzoyloxy)-10,11-dihydro-5H-dibenz/b,f/azepine-5-carboxamide
(4) 10-(3-methoxybenzoyloxy)-10,11-dihydro-5H-dibenz/b,f/azepine-5-carboxamide
(5) 10-(2-methoxybenzoloxy)-10,11-dihydro-5H-dibenz/b,f/azepine-5-carboxamide
(6) 10-(4-nitrobenzoyloxy)-10,11-dihydro-5H-dibenz/b,f/azepine-5-carboxamide
(7) 10-(3-nitrobenzoyloxy)-10,11-dihydro-5H-dibenz/b,f/azepine-5-carboxamide
(8) 10-(2-nitrobenzoyloxy)-10,11-dihydro-5H-dibenz/b,f/azepine-5-carboxamide
(9) 10-(4-chlorobenzoyloxy)-10,11-dihydro-5H-dibenz/b,f/azepine-5-carboxamide
(10) 10-(3-chlorobenzoyloxy)-10,11-dihydro-5H-dibenz/b,f/azepine-5-carboxamide
(11) 10-(2-acetoxybenzoyloxy)-10,11-dihydro-5H-dibenz/b,f/azepine-5-carboxamide
(12) 10-propionyloxy-10,11-dihydro-5H-dibenz/b,f/azepine-5-carboxamide
(13) 10-butyryloxy-10,1-dihydro-5H-dibenz/b,f/azepine-5-carboxamide
(14) 10-pivaloyloxy-10,11-dihydro-5H-dibenz/b,f/azepine-5-carboxamide
(15) 10-[(2-propyl)pentanoyloxy]-10,11-dihydro-5H-dibenz/b,f/azepine-5-carboxamide
(16) 10-[(2-ethyl)hexanoyloxy]-10,11-dihydro-5H-dibenz/b,f/azepine-5-carboxamide
(17) 10-stearoyloxy-10,11-dihydro-5H-dibenz/b,f/azepine-5-carboxamide
(18) 10-cyclopentanoyloxy-10,11-dihydro-5H-dibenz/b,f/azepine-5-carboxamide
(19) 10-cyclohexanoyloxy-10,11-dihydro-5H-dibenz/b,f/azepine-5-carboxamide
(20) 10-phenylacetoxy-10,11-dihydro-5H-dibenz/b,f/azepine-5-carboxamide
(21) 10-(4-methoxyphenyl)acetoxy-10,11-dihydro-5H-dibenz/b,f/-azepine-5-carboxamide
(22) 10-(3-methoxyphenyl)acetoxy-10,11-dihydro-5H-dibenz/b,f/azepine-5-carboxamide
(23) 10-(4-nitrophenyl)acetoxy-10,11-dihydro-5H-dibenz/b,f/azepine-5-carboxamide
(24) 10-(3-nitrophenyl)acetoxy-10,11-dihydro-5H-dibenz/b,f/azepine-5-carboxamide
(25) 10-nicotinoyloxy-10,11-dihydro-5H-dibenz/b,f/azepine-5-carboxamide
(26) 10-isonicotinoyloxy-10,11-dihydro-5H-dibenz/b,f/azepine-5-carboxamide
(27) 10-chloroacetoxy-10,11-dihydro-5H-dibenz/b,f/azepine-5-carboxamide
(28) 10-bromoacetoxy-10,11-dihydro-5H-dibenz/b,f/azepine-5-carboxamide
(29) 10-formyloxy-10,11-dihydro-5H-dibenz/b,f/azepine-5-carboxamide
(30) 10-ethoxycarbonyloxy-10,11-dihydro-5H-dibenz/b,f/azepine-5-carboxamide
(31) 10-(2-chloropropionyloxy)-10,11-dihydro-5H-dibenz/b,f/azepine-5-carboxamide The compounds of formula IA and IB produced according to the process of the present invention may be used as an API and formulated into finished pharmaceutical products, or may be converted by further chemical transformation to another API.

The following non-limiting examples illustrate the processes and uses of the present invention.

EXAMPLES

Preparation of Enol Acetate (R=Methyl)

To a suspension of oxcarbazepine (69.3 g, 0.275 mol), DMAP (1.025 g) and acetic anhydride (38.07 g) in dichloromethane (700 mL) was added drop wise a solution of 30.1 g pyridine in 50 mL dichloromethane at room temperature. The addition completed in 10 min. After stirring at room temperature for 75 min, the system became clear. Three hours after the addition, the system became cloudy again. The suspension was then stirred at room temperature for one more hour and washed with 2×400 mL of 1 N HCl, 2×400 mL of 10% $NaHCO_3$ and 2×400 mL of $H_2O$. Concentration under reduced pressure afforded a light yellow solid. Isopropyl alcohol (700 mL) was added and the mixture was refluxed for 3 min. When it cooled down, the solid was filtered off and washed with 2×100 mL isopropyl alcohol. Isopropyl alcohol (500 mL) was added and the mixture was refluxed for 2 min. When it cooled down, the solid was filtered off and washed with 3×100 mL isopropyl alcohol (This second wash may not be necessary). The final product was dried under vacuum and obtained as a white solid (71.5 g) in 88% yield. 1H NMR (DMSO-d6, 360 MHz):δ=7.53-7.30 (m, 8H), 6.92 (s, 1H), 5.66 (b, 2H), 2.32 (s, 3H) ppm. 13C NMR (DMSO-d6, 90 MHz): δ=169.5, 156.2, 146.8, 140.7, 140.4, 132.8, 132.1, 131.1, 129.8, 129.7, 129.4, 127.9, 127.6, 125.9, 120.8, 21.1 ppm.

Preparation of Rh(COD)(RcSp-DuanPhos)$BF_4$

In a 1 L three-neck round bottom flask, 27.2 g RcSp-DuanPhos was dissolved in 200 mL of dichloromethane and the solution was bubbled with nitrogen for 10 min. 29.0 g of Rh(COD)$_2$$BF_4$ was added in one portion and the mixture was stirred at room temperature for 1 h. To the reddish solution was added hexanes (400 mL) slowly. Orange solid precipitated out. It was stirred for 30 min and filtered, and washed with hexane. The orange solid was dried in vacuum and gave 47.2 g product in 97% yield. The product was stored under nitrogen.

General Procedure for Asymmetric Hydrogenation

A 300 mL-volume autoclave with glass vial (20 mL) was charged with substrate (enol acetate: compound II, R=methyl), catalyst as well as 3-5 ml oxygen-free solvent under nitrogen. The autoclave was charged with hydrogen to the desired pressure and stirred at room temperature or heated with an oil bath. After hydrogen was released carefully, the reaction mixture was concentrated and purified by a flash column, which was eluted with methanol. This sample was used for chiral HPLC analysis.

Analytical Technique

Enantiomeric excess (% ee) of the product of hydrogenation (S-(−)- or R-(+)-licarbazepine acetate: compound IA or IB, R=methyl)) was determined by HPLC analysis using the following parameters.

Flow Rate: 1 mL/min
Detection: UV@210 nm

Retention Time R-(+)-licarbazepine acetate: 20 min
Retention Time of eslicarbazepine acetate: 24 min
Retention Time of enol acetate: 42-50 min Reactions were carried out in accordance with the General Procedure for Asymmetric Hydrogenation using various catalysts, solvents, pressures and temperatures, giving the following results.

TABLE 1

Rh(I)/TangPhos Catalyzed Asymmetric Hydrogenation

| Catalyst | Solvent | $H_2$ (psi) | Ee (%) | Conf. |
|---|---|---|---|---|
| [Rh(NBD)(SSRR-TangPhos)]$BF_4$ | EtOAc | 20 | 86 | S |
| [Rh(NBD)(SSRR-TangPhos)]$BF_4$ | MeOH | 20 | 50 | S |
| [Rh(NBD)(SSRR-TangPhos)]$BF_4$ | THF | 20 | 73 | S |
| [Rh(NBD)(SSRR-TangPhos)]$BF_4$ | $CH_2Cl_2$ | 20 | 28 | S |
| [Rh(NBD)(SSRR-TangPhos)]$BF_4$ | THF | 150 | 73 | S |
| [Rh(NBD)(SSRR-TangPhos)]$BF_4$ | EtOAc | 150 | 81 | S |
| [Rh(COD)(SSRR-TangPhos)]$BF_4$ | THF | 150 | 78 | S |
| [Rh(COD)(SSRR-TangPhos)]$BF_4$ | MeOAc | 750 | 66 | S |

All reactions were carried out at room temperature.

TABLE 2

Rh(I)/DuanPhos Catalyzed Asymmetric Hydrogenation - Solvent Effect

| Catalyst | Solvent | $H_2$ (psi) | Ee (%) | Conf. |
|---|---|---|---|---|
| [Rh(NBD)(RcSp-DuanPhos)]$BF_4$ | EtOAc | 20 | 93 | S |
| [Rh(NBD)(ScRp-DuanPhos)]$BF_4$ | MeOH | 20 | 55 | R |
| [Rh(NBD)(ScRp-DuanPhos)]$BF_4$ | EtOAc | 20 | 91 | R |
| [Rh(NBD)(ScRp-DuanPhos)]$BF_4$ | THF | 20 | 92 | R |
| [Rh(NBD)(ScRp-DuanPhos)]$BF_4$ | $CH_2Cl_2$ | 20 | 90 | R |
| [Rh(COD)(RcSp-DuanPhos)]$BF_4$ | EtOAc | 750 | 94 | S |
| [Rh(COD)(RcSp-DuanPhos)]$BF_4$ | EtOAc/THF | 750 | 93 | S |
| [Rh(COD)(RcSp-DuanPhos)]$BF_4$ | THF | 750 | 93 | S |
| [Rh(COD)(RcSp-DuanPhos)]$BF_4$ | MeOAc | 750 | 89 | S |
| [Rh(COD)(RcSp-DuanPhos)]$BF_4$ | MeTHF | 750 | 94 | S |
| [Rh(COD)(RcSp-DuanPhos)]$BF_4$ | $CF_3CH_2OH$ | 750 | 26 | S |

All reactions were carried out at room temperature.

TABLE 3

[Rh(COD)(RcSp-DuanPhos)]$BF_4$ Catalyzed Asymmetric Hydrogenation - Solvent Effect

| Solvent | Ee (%) |
|---|---|
| THF/DMF 9:1 | 85 |
| $CH_2Cl_2$/DMF 9:1 | 83 |
| EtOAc/DMF 9:1 | 92 |
| THF/EtOH 9:1 | 92 |
| EtOAc/EtOH 9:1 | 88 |
| THF/MeOH 8:2 | 90 |
| THF/$CF_3CH_2OH$ 9:1 | 90.3 |
| THF/$CF_3CH_2OH$ 8:2 | 89.5 |
| THF/$CF_3CH_2OH$ 7:3 | 85.7 |
| THF/$CF_3CH_2OH$ 6:4 | 80.9 |
| THF/$CF_3CH_2OH$ 5:5 | 77.1 |
| $CH_2Cl_2$/MeOH 8:2 | 80 |
| $CH_2Cl_2$/$CF_3CH_2OH$ 9:1 | 61 |
| EtOAc/$CF_3CH_2OH$ 8:2 | 84 |
| 1,4-dioxane** | 89 |

*All reactions other than ** were carried out under 750 psi of hydrogen at room temperature.
**1000 psi.

TABLE 4

Rh(I)/DuanPhos Catalyzed Asymmetric Hydrogenation - Pressure Effect

| Catalyst | Solvent | H₂ (psi) | Ee (%) | Conf. |
|---|---|---|---|---|
| [Rh(NBD)(RcSp-DuanPhos)]BF₄ | EtOAc | 20 | 93 | S |
| [Rh(NBD)(RcSp-DuanPhos)]BF₄ | EtOAc | 150 | 91 | S |
| [Rh(NBD)(RcSp-DuanPhos)]BF₄ | THF | 150 | 92 | S |
| [Rh(NBD)(ScRp-DuanPhos)]BF₄ | THF | 20 | 92 | R |
| [Rh(COD)(RcSp-DuanPhos)]BF₄ | EtOAc | 1000 | 92 | S |
| [Rh(COD)(RcSp-DuanPhos)]BF₄ | EtOAc | 750 | 94 | S |
| [Rh(COD)(RcSp-DuanPhos)]BF₄ | EtOAc | 150 | 91 | S |
| [Rh(COD)(RcSp-DuanPhos)]BF₄ | EtOAc | 20 | 89 | S |
| [Rh(COD)(RcSp-DuanPhos)]BF₄ | EtOAc/THF 1:1 | 750 | 93 | S |
| [Rh(COD)(RcSp-DuanPhos)]BF₄ | EtOAc/THF 1:1 | 150 | 91 | S |
| [Rh(COD)(RcSp-DuanPhos)]BF₄ | THF | 1000 | 92 | S |
| [Rh(COD)(RcSp-DuanPhos)]BF₄ | THF | 750 | 93 | S |
| [Rh(COD)(RcSp-DuanPhos)]BF₄ | THF | 500 | 92 | S |
| [Rh(COD)(RcSp-DuanPhos)]BF₄ | THF | 150 | 92 | S |
| [Rh(COD)(RcSp-DuanPhos)]BF₄ | THF | 20 | 92 | S |
| [Rh(COD)(RcSp-DuanPhos)]BF₄ | CH₂Cl₂ | 1000 | 67 | S |
| [Rh(COD)(RcSp-DuanPhos)]BF₄ | CH₂Cl₂ | 750 | 74 | S |
| [Rh(COD)(RcSp-DuanPhos)]BF₄ | CH₂Cl₂ | 20 | 81 | S |

All reactions were carried out at room temperature.

TABLE 5

Rh(I)/DuanPhos Catalyzed Asymmetric Hydrogenation - Temperature Effect

| Catalyst | Solvent | H₂ (psi) | Temp (°C.) | Ee (%) |
|---|---|---|---|---|
| [Rh(COD)(RcSp-DuanPhos)]BF₄ | THF | 750 | rt | 93 |
| [Rh(COD)(RcSp-DuanPhos)]BF₄ | THF | 750 | 0 | 93 |
| [Rh(COD)(RcSp-DuanPhos)]BF₄ | THF | 750 | 40-50 | 74 |
| [Rh(NBD)(RcSp-DuanPhos)]BF₄ | THF | 750 | 40-50 | 66 |
| [Rh(COD)(SSRR-TangPhos)]BF₄ | THF | 750 | 40-50 | 67 |

It will be appreciated that the invention may be modified within the scope of the appended claims.

The invention claimed is:

1. A process for preparing a compound of the formula IA or IB:

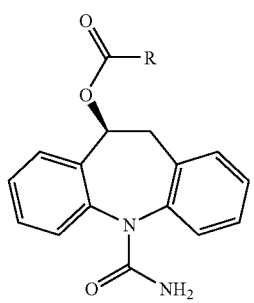

IA

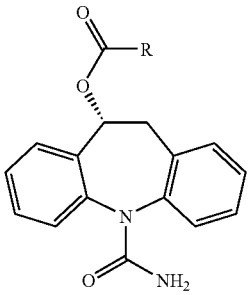

IB wherein R is alkyl, aminoalkyl, halogenalkyl, aralkyl, cycloalkyl, cycloalkylalkyl, alkoxy, phenyl or substituted phenyl or pyridyl group; the term alkyl means carbon chain, straight or branched, containing from 1 to 18 carbon atoms; the term halogen represents fluorine, chlorine, bromine or iodine; the term cycloalkyl represents a saturated alicyclic group with 3 to 6 carbon atoms; the term aryl represents unsubstituted phenyl group or phenyl substituted by alkoxy, halogen or nitro group, the process comprising asymmetric hydrogenation of a compound of the formula II:

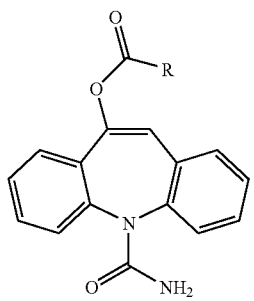

II wherein R has the same meanings as above, using a chiral catalyst and a source of hydrogen.

2. The process according to claim 1, wherein R is $C_1$ to $C_3$ alkyl.

3. The process according to claim 2, wherein R is methyl.

4. The process according to claim 1, wherein the compound of formula IA or IB is the S or R enantiomer, respectively, of:
   (1) 10-acetoxy-10,11-dihydro-5H-dibenz/b,f/azepine-5-carboxamide
   (2) 10-benzoyloxy-10,11-dihydro-5H-dibenz/b,f/azepine-5-carboxamide
   (3) 10-(4-methoxybenzoyloxy)-10,11-dihydro-5H-dibenz/b,f/azepine-5-carboxamide
   (4) 10-(3-methoxybenzoyloxy)-10,11-dihydro-5H-dibenz/b,f/azepine-5-carboxamide
   (5) 10-(2-methoxybenzoyloxy)-10,11-dihydro-5H-dibenz/b,f/azepine-5-carboxamide
   (6) 10-(4-nitrobenzoyloxy)-10,11-dihydro-5H-dibenz/b,f/azepine-5-carboxamide
   (7) 10-(3-nitrobenzoyloxy)-10,11-dihydro-5H-dibenz/b,f/azepine-5-carboxamide
   (8) 10-(2-nitrobenzoyloxy)-10,11-dihydro-5H-dibenz/b,f/azepine-5-carboxamide
   (9) 10-(4-chlorobenzoyloxy)-10,11-dihydro-5H-dibenz/b,f/azepine-5-carboxamide
   (10) 10-(3-chlorobenzoyloxy)-10,11-dihydro-5H-dibenz/b,f/azepine-5-carboxamide

(11) 10-(2-acetoxybenzoyloxy)-10,11-dihydro-5H-dibenz/b,f/azepine-5-carboxamide
(12) 10-propionyloxy-10,11-dihydro-5H-dibenz/b,f/azepine-5-carboxamide
(13) 10-butyryloxy-10,1-dihydro-5H-dibenz/b,f/azepine-5-carboxamide
(14) 10-pivaloyloxy-10,11-dihydro-5H-dibenz/b,f/azepine-5-carboxamide
(15) 10-[(2-propyl)pentanoyloxy]-10,11-dihydro-5H-dibenz/b,f/azepine-5-carboxamide
(16) 10-[(2-ethyl)hexanoyloxy]-10,11-dihydro-5H-dibenz/b,f/azepine-5-carboxamide
(17) 10-stearoyloxy-10,11-dihydro-5H-dibenz/b,f/azepine-5-carboxamide
(18) 10-cyclopentanoyloxy-10,11-dihydro-5H-dibenz/b,f/azepine-5-carboxamide
(19) 10-cyclohexanoyloxy-10,11-dihydro-5H-dibenz/b,f/azepine-5-carboxamide
(20) 10-phenylacetoxy-10,11-dihydro-5H-bibenz/b,f/azepine-5-carboxamide
(21) 10-(4-methoxyphenyl)acetoxy-10,11-dihydro-5H-dibenz/b,f/-azepine-5-carboxamide
(22) 10-(3-methoxyphenyl)acetoxy-10,11-dihydro-5H-dibenz/b,f/azepine-5-carboxamide
(23) 10-(4-nitrophenyl)acetoxy-10,11-dihydro-5H-dibenz/b,f/azepine-5-carboxamide
(24) 10-(3-nitrophenyl)acetoxy-10,11-dihydro-5H-dibenz/b,f/azepine-5-carboxamide
(25) 10-nicotinoyloxy-10,11-dihydro-5H-dibenz/b,f/azepine-5-carboxamide
(26) 10-isonicotinoyloxy-10,11-dihydro-5H-dibenz/b,f/azepine-5-carboxamide
(27) 10-chloroacetoxy-10,11-dihydro-5H-dibenz/b,f/azepine-5-carboxamide
(28) 10-bromoacetoxy-10,11-dihydro-5H-dibenz/b,f/azepine-5-carboxamide
(29) 10-formyloxy-10,11-dihydro-5H-dibenz/b,f/azepine-5-carboxamide
(30) 10-ethoxycarbonyloxy-10,11-dihydro-5H-dibenz/b,f/azepine-5-carboxamide
(31) 10-(2-chloropropionyloxy)-10,11-dihydro-5H-dibenz/b,f/azepine-5-carboxamide.

5. The process according to claim 1, wherein the chiral catalyst is a complex of rhodium.

6. The process according to claim 5, wherein the chiral catalyst is selected from Rh(I) complexes having chiral ligands with the following structures:

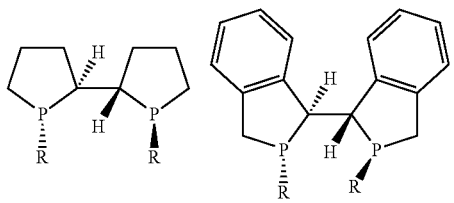

and their stereosiomers, wherein R' is selected from alkyl, aryl, substituted alkyl, substituted aryl, hetereoaryl, ferrocenyl, alkoxy and aryloxy.

7. The process according to claim 6, wherein R' is selected from $CH_3$, Et, i-Pr, t-Bu, 1-adamantyl, $Et_3C$, cyclo-$C_5H_9$, cyclo-$C_6H_{11}$, phenyl, p-tolyl, 3,5-dimethylphenyl, 3,5-di-t-butylphenyl, ortho-anisyl and naphthyl.

8. The process according to claim 7, wherein R' is t-Bu.

9. The process according to claim 1, wherein the chiral catalyst is selected from a stereoisomer of [Rh(norbornadiene)(DuanPhos)]$BF_4$, [Rh($\eta$-1,5-cyclooctadiene)(DuanPhos)]$BF_4$, [Rh(norbornadiene)(TangPhos)]$BF_4$ and [Rh($\eta$-1,5-cyclooctadiene)(TangPhos)]$BF_4$, wherein the ScRp-DuanPhos and RRSS-TangPhos stereosiomers have the following chemical structures:

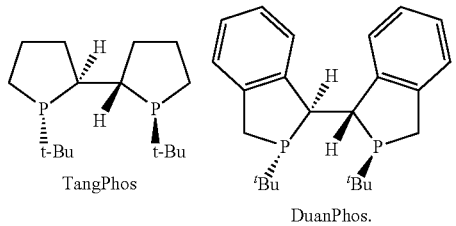

10. The process according to claim 9, wherein the chiral catalyst is selected from [Rh(norbornadiene)(SSRR-TangPhos)]$BF_4$, [Rh($\eta$-1,5-cyclooctadiene) (SSRR-TangPhos)]$BF_4$, [Rh(norbornadiene)(RcSp-DuanPhos)]$BF_4$, [Rh(norbornadiene)(ScRp-DuanPhos)]$BF_4$, [Rh($\eta$-1,5-cyclooctadiene)(RcSp-DuanPhos)]$BF_4$, [Rh(norbornadiene) (RRSS -TangPhos)]$BF_4$, [Rh($\eta$-1,5-cyclooctadiene)(RRSS-TangPhos)]$BF_4$ and [Rh($\eta$-1,5-cyclooctadiene)(ScRp-DuanPhos)]$BF_4$.

11. The process according to claim 1, wherein the source of hydrogen is hydrogen gas.

12. The process according to claim 1, wherein the molar ratio of compound II to catalyst is from 1:1 to 50,000:1.

13. The process according to claim 12, wherein the molar ratio of compound II to catalyst is 500:1.

14. The process according to claim 13, wherein the molar ratio of compound II to catalyst is 50:1.

15. The process according to claim 1, wherein the asymmetric hydrogenation is carried out at a temperature from 0° C. to room temperature.

16. The process according to claim 15, wherein the asymmetric hydrogenation is carried out at room temperature.

17. The process according to claim 1, wherein the asymmetric hydrogenation is carried out at a pressure of 20 psi to 1000 psi.

18. The process according to claim 17, wherein the asymmetric hydrogenation is carried out at a pressure of 750 psi to 1000 psi.

19. The process according to claim 1, wherein the compound of formula II is dissolved in a solvent selected from methanol, ethanol, THF, 2-methyl-THF, methyl acetate, ethyl acetate, dichloromethane, trifluoroethanol, 1,4-dioxane, DMF and mixtures thereof.

20. The process according to claim 19, wherein the catalyst is Rh(NBD)(SSRR-TangPhos)$BF_4$ and the solvent is ethyl acetate.

21. The process according to claim 19, wherein the catalyst is [Rh(NBD)(RcSp-DuanPhos)]$BF_4$ or [Rh(NBD)(ScRp-DuanPhos)]$BF_4$ and the solvent is ethyl acetate, THF or dichloromethane.

22. The process according to claim 19, wherein the catalyst is [Rh(COD)(RcSp-DuanPhos)]$BF_4$ and the solvent is ethyl acetate, THF, 2-methyl-THF, or a mixture thereof.

23. The process according to claim 22, wherein the solvent is THF.

24. The process according to claim 1, wherein the compound of formula II is prepared from oxcarbazepine.

25. The process according to claim 24, wherein the oxcarbazepine is reacted with an anhydride of the formula R—C(O)—O—C(O)—R, in the presence of a base and a catalyst, wherein R is alkyl, aminoalkyl, halogenalkyl, aralkyl, cycloalkyl, cycloalkylalkyl, alkoxy, phenyl or substituted phenyl or pyridyl group; the term alkyl means carbon chain, straight or branched, containing from 1 to 18 carbon atoms; the term halogen represents fluorine, chlorine, bromine or iodine; the term cycloalkyl represents a saturated alicyclic group with 3 to 6 carbon atoms; the term aryl represents unsubstituted phenyl group or phenyl substituted by alkoxy, halogen or nitro group.

26. The process according to claim 25, wherein the base is pyridine.

27. The process according to claim 25, wherein the catalyst is DMAP.

28. A process for preparing (S)-(−)-10-acetoxy-10,11-dihydro-5H-dibenz/b,f/azepine-5-carboxamide comprising asymmetric hydrogenation of the compound of the formula II:

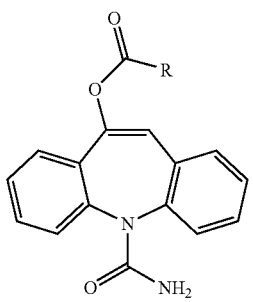

wherein R is alkyl, aminoalkyl, halogenalkyl, aralkyl, cycloalkyl, cycloalkylalkyl, alkoxy, phenyl or substituted phenyl or pyridyl group; the term alkyl means carbon chain, straight or branched, containing from 1 to 18 carbon atoms; the term halogen represents fluorine, chlorine, bromine or iodine; the term cycloalkyl represents a saturated alicyclic group with 3 to 6 carbon atoms; the term aryl represents unsubstituted phenyl group or phenyl substituted by alkoxy, halogen or nitro group.

29. The process according to claim 1, further comprising combining the compound of formula IA or IB with one or more pharmaceutically acceptable carriers and/or one or more pharmaceutically acceptable excipients to form a pharmaceutical composition.

30. The process according to claim 1, further comprising converting the compound of formula IA to (S)-(+)-MHD, or the compound of formula IB to (R)-(−)-MHD, by deesterification.

31. A process for preparing a compound of formula II:

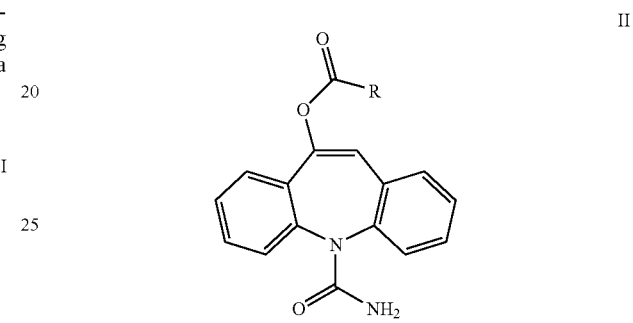

wherein R is $CH_3$, comprising reacting oxcarbazepine with acetic anhydride in the presence of a base and a catalyst.

32. The process according to claim 31, wherein the base is pyridine.

33. The process according to claim 31, wherein the catalyst is DMAP.

34. The process according to claim 28, wherein R is methyl.

* * * * *

UNITED STATES PATENT AND TRADEMARK OFFICE
CERTIFICATE OF CORRECTION

PATENT NO. : 8,367,821 B2  Page 1 of 1
APPLICATION NO. : 12/294855
DATED : February 5, 2013
INVENTOR(S) : Yu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1033 days.

Signed and Sealed this

First Day of September, 2015

Michelle K. Lee
*Director of the United States Patent and Trademark Office*